United States Patent
Park et al.

(10) Patent No.: US 8,211,174 B2
(45) Date of Patent: Jul. 3, 2012

(54) TRANSTYMPANIC VIBRATION DEVICE FOR IMPLANTABLE HEARING AID AND APPARATUS FOR INSTALLING THE SAME

(76) Inventors: Il Yong Park, Chungcheongnam-do (KR); Seung Ha Lee, Chungcheongnam-do (KR)

( * ) Notice: Subject to any disclaimer, the term of this patent is extended or adjusted under 35 U.S.C. 154(b) by 402 days.

(21) Appl. No.: 12/333,263

(22) Filed: Dec. 11, 2008

(65) Prior Publication Data
US 2010/0010628 A1      Jan. 14, 2010

(30) Foreign Application Priority Data
Jul. 8, 2008   (KR) .................. 10-2008-0066061

(51) Int. Cl.
*A61F 2/18* (2006.01)
(52) U.S. Cl. .................. 623/10; 600/25; 607/57
(58) Field of Classification Search .............. 623/10; 607/57; 600/25
See application file for complete search history.

(56) References Cited

U.S. PATENT DOCUMENTS

| | | | |
|---|---|---|---|
| 4,817,607 A * | 4/1989 | Tatge .................. | 623/10 |
| 4,840,178 A * | 6/1989 | Heide et al. .................. | 600/25 |
| 4,936,305 A * | 6/1990 | Ashtiani et al. .................. | 607/57 |
| 4,957,478 A * | 9/1990 | Maniglia .................. | 600/25 |
| 5,220,918 A * | 6/1993 | Heide et al. .................. | 600/25 |
| 5,624,376 A * | 4/1997 | Ball et al. .................. | 600/25 |
| 6,171,229 B1 * | 1/2001 | Kroll et al. .................. | 600/25 |
| 6,387,039 B1 * | 5/2002 | Moses .................. | 600/25 |
| 6,475,134 B1 * | 11/2002 | Ball et al. .................. | 600/25 |
| 6,671,559 B2 * | 12/2003 | Goldsmith et al. .................. | 607/57 |
| 7,174,214 B2 * | 2/2007 | Seligman .................. | 607/57 |
| 2004/0093040 A1 * | 5/2004 | Boylston et al. .................. | 607/57 |
| 2008/0319250 A1 * | 12/2008 | Asnes .................. | 600/25 |
| 2009/0043149 A1 * | 2/2009 | Abel .................. | 600/25 |
| 2009/0281397 A1 * | 11/2009 | Lavoisier .................. | 600/301 |

* cited by examiner

*Primary Examiner* — Paul Prebilic
(74) *Attorney, Agent, or Firm* — Law Offices of Robert F. Sielinski, LLC

(57) ABSTRACT

A transtympanic vibration device for an implantable healing aid, suitable for being vibrated by magnetic flux transmitted from an outside and transferring vibration to a tympanic membrane. The device includes an outer plate having one surface on which a detachable magnet is detachably arranged; an inner plate sandwiching the tympanic membrane in cooperation with the outer plate and having a on which a fixed magnet is arranged; and at least one connection member connecting the outer plate and the inner plate with each other in such a manner that a distance between the outer plate and the inner plate can be adjusted.

14 Claims, 16 Drawing Sheets

TRANSTYMPANIC VIBRATION DEVICE FOR IMPLANTABLE HEARING AID AND APPARATUS FOR INSTALLING THE SAME

CLAIM OF PRIORITY

This application claims the benefit of Korean Patent Application No. 10-2008-0066061 filed Jul. 8, 2008, in the Korean Intellectual Property Office, the disclosure of which is incorporated herein by reference.

BACKGROUND OF THE INVENTION

1. Field of the Invention

The present invention relates to a transtympanic vibration device for an implantable healing aid and an apparatus for installing the same.

2. Description of the Related Art

As is generally known, because the ear is one of the important sense organs of the human body, a person may feel inconvenience when one cannot hear well due to the degradation of the sensitivity of the ear. In the case of hardness of heating, while most patients solve the problem using hearing aids, the effects of the hearing aids are not so substantial. The reason for this is that the conventional healing aids have defects in terms of performance.

The conventional hearing aids are an air conduction type in which a sound signal is first converted into an electrical signal that is then converted again into a sound signal through amplification and signal processing and is transmitted to a user. Since the conventional hearing aids have a limited sound transmitting characteristic of about 4 kHz or below, speech discrimination in noisy circumstances degrades. Further, due to the structural problems of the hearing aids, a distortion phenomenon can occur so that the quality of sound may not be satisfactory. Also, in the case of increasing the gain of the hearing aids to be used for a person who has difficulties in hearing and possesses a high speech reception threshold, because a howling phenomenon conspicuously occurs due to sound feedback, the limiting range of gain cannot but be narrowed.

In order to cope with these problems caused in the conventional air conduction type hearing aids, an implantable middle ear hearing device (IMEHD) as one of implantable hearing aids has been researched and developed in advanced nations including the U.S.A., Japan and European countries.

The implantable middle ear hearing device does not adopt the air conduction type in which sound is transmitted to a middle ear through a microphone, an amplifier, a speaker (a receiver), an external auditory canal, a tympanic membrane and ear ossicles, but adopts a manner in which vibration is directly transferred to a middle ear through a microphone, an amplifier, a vibration element and ear ossicles. Thus, the implantable middle ear hearing device is evaluated as a hearing aid which has an excellent high frequency transmitting characteristic and solves the problems of the conventional hearing aids such as the howling phenomenon.

A typical implantable middle ear hearing device, which is successfully commercialized at the present time, is the Soundbridge manufactured by Vibrant Medel of Austria. The vibration element used in the Soundbridge is an FMT (floating mass transducer) in which a coil and a magnet are assembled integrally with each other. The vibration element is mounted to the malleus of ear ossicles through surgical operation including the drilling of a temporal bone. An electrical signal corresponding to a sound signal is applied through the coil to directly induce vibration, and a sound signal is transmitted to the cochlea.

While this type of implantable middle ear heating device is currently known, through clinical experiments, as an implantable hearing aid which is effective to persons suffering from intermediate and high grades of sensorineural heating loss, it has disadvantages in that the operation is complicated and a substantial cost is incurred. Also, it has a problem in that the ear ossicles are likely to be adversely influenced by the vibration element which is directly clamped to the ear ossicles.

In another type, a vibrational element for an implantable middle ear hearing device has been proposed by Soundtec of the U.S.A. Because this vibrational element adopts a scheme in which a micro magnet having mounted thereto a ring for connecting ear ossicles is installed between the malleus and the stapes of the ear ossicles, operation is further complicated as compared to the Soundbridge. Moreover, since the distance between the magnet installed on the ear ossicles and the outside coil located in the external auditory canal is substantial, an increased amount of current should be supplied to the outside coil, which leads to a problem.

In addition to the vibrational elements for implantable hearing aids, which can be installed through the complicated and difficult operation as described above, other vibrational elements, which can be installed with no or minimal operativity, have been disclosed in the art.

Heide, et al. have disclosed a vibrational element in which a hole is defined in the manibrium of the malleus among the three bones constituting the ear ossicles and the magnet positioned in the external auditory canal is connected with and coupled to the manibrium of the malleus by mechanical coupling means such as a screw. Of course, the vibrational element is also vibrated by an outside coil.

In the vibrational element of Heide, et al, although an operational procedure such as the drilling of the temporal bone is not required, a problem results because a highly precise operation should be conducted in order to define a fine hole of less than 1 mm and to connect the magnet with the manibrium of the malleus. Furthermore, side effects are likely to result due to the breakage of paths which are defined in the malleus and through which nerves, blood and body fluids pass.

Meanwhile, Resound as an American hearing aid manufacturer has suggested a tympanic membrane attachment type vibrational element which is composed of a polymeric layer similar to a contact lens and a magnet. The polymeric layer having the shape of a dish, on which the magnet is placed, is attached to the surface of the tympanic membrane with the aid of silicon or polymer oil which is harmless to the human body. As the magnet is vibrated by an outside coil, sound is transmitted.

This type of vibrational element is being actively researched at Stanford University, etc. in the U.S.A. as an alternative for the implantable hearing aids, which can solve the problems caused due to the limited high frequency characteristic of the conventional hearing aids while not imposing a burden onto a patient since operating is not required.

However, in this type of vibrational element, the surface contour of the tympanic membrane should be fundamentally considered when forming the polymeric layer, and the oil for attaching the polymeric layer should be periodically supplied.

SUMMARY OF THE INVENTION

Accordingly, the present invention has been made keeping in mind the above problems occurring in the related art and an object of the present invention is to provide a vibration device which can be simply installed on and removed from a tympanic membrane or a malleus such that it can stably conform to the surface contour and the thickness of the tympanic membrane that may be different from person to person.

Another object of the present invention is to provide an apparatus which can easily install the vibration device on the tympanic membrane.

In order to achieve the first object, according to one aspect of the present invention, there is provided a transtympanic vibration device for an implantable hearing aid, suitable for being vibrated by magnetic flux transmitted from an outside and transferring vibration to a tympanic membrane, the device comprising an outer plate having one surface on which a detachable magnet is detachably arranged; an inner plate sandwiching the tympanic membrane in cooperation with the outer plate and having a on which a fixed magnet is arranged; and at least one connection member connecting the outer plate and the inner plate with each other in such a manner that a distance between the outer plate and the inner plate can be adjusted.

According to another aspect of the present invention, magnetic force of the fixed magnet is applied to an external auditory canal through the tympanic membrane.

According to another aspect of the present invention, a mounting part is formed on the outer plate to allow the detachable magnet to be arranged thereon.

According to another aspect of the present invention, the connection member is installed to be securely fastened to one of the outer plate and the inner plate and to pass through the other of the outer plate and the inner plate.

According to another aspect of the present invention, a soft substance is provided to surfaces of the outer plate and the inner plate which come into contact with the tympanic membrane.

According to another aspect of the present invention, a seating part is formed on an outer surface of the inner plate to increase a contact area between the inner plate and a malleus.

According to another aspect of the present invention, a clip element is installed on an outer surface of the inner plate to be coupled to a malleus.

According to another aspect of the present invention, the clip element is kept elastically diverged by the magnetic force of the fixed plate and converges and is coupled to the malleus when the detachable magnet is arranged on the outer plate.

According to another aspect of the present invention, the clip element is made of a shape memory material which converges by heat from a human body.

According to another aspect of the present invention, when the tympanic membrane projects toward a middle ear cavity, the outer plate comprises a thin soft layer so as to increase adhesive force between the outer plate and the tympanic membrane having a certain surface contour.

According to another aspect of the present invention, when the tympanic membrane projects toward a middle ear cavity, the outer plate comprises a spiral plate which has a diameter gradually decreasing toward a center thereof.

According to another aspect of the present invention, at least two connection members are provided to be spaced apart by a predetermined interval on the outer plate and the inner plate.

According to another aspect of the present invention, one connection member is provided.

In order to achieve the first object, according to another aspect of the present invention, there is provided a transtympanic vibration device for an implantable hearing aid, suitable for being vibrated by magnetic flux transmitted from an outside and transferring vibration to a tympanic membrane, the device comprising an outer plate having one surface on which a detachable magnet is detachably arranged; an extended part extending from the outer plate through the tympanic membrane toward a middle ear cavity; and a clip element having one end which is coupled to the extended part such that it is elastically diverged outward and the other end on which a fixed magnet is arranged such that the clip element can converge and be coupled to a malleus by attractive force produced between the detachable magnet and the fixed magnet.

In order to achieve the second object, according to still another aspect of the present invention, there is provided an apparatus for installing or removing a transtympanic vibration device on or from a tympanic membrane, the apparatus comprising a hollow guide member having a length that extends from an ear hole to the tympanic membrane; a movable member inserted into the guide member; a magnetic force production part installed on a distal end of the movable member and producing magnetic force when electric power is applied thereto; and a power source part supplying electric power to the magnetic force production part.

According to a still further aspect of the present invention, a paramagnet is embedded in a center portion of the magnetic force production part to gather lines of magnetic force.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF PREFERRED EMBODIMENTS

Figure 1:
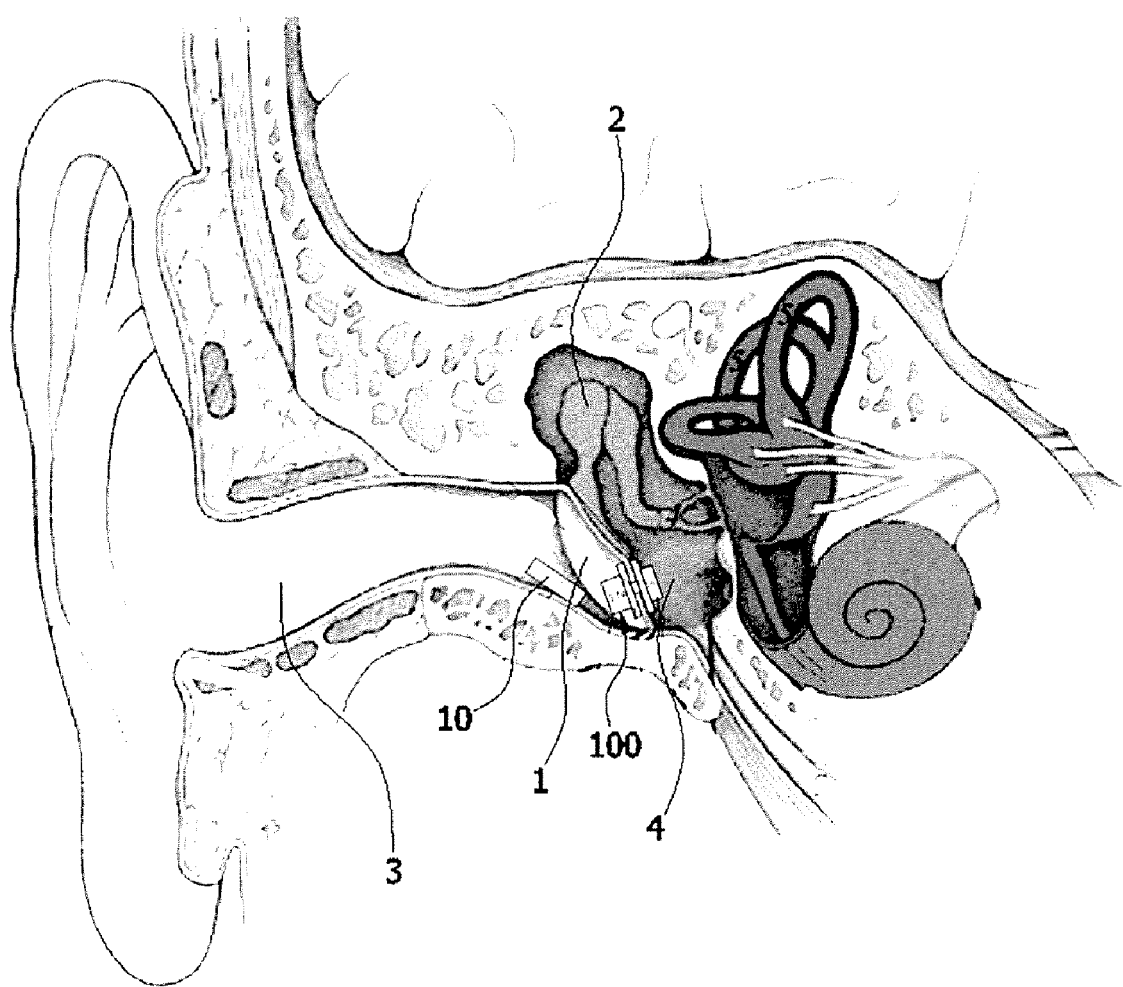
FIG. 1 is a view illustrating the state in which a transtympanic vibration device according to the present invention is installed on a tympanic membrane.

Reference will now be made in greater detail to the preferred embodiments of the invention, examples of which are illustrated in the accompanying drawings. Wherever possible, the same reference numerals will be used throughout the drawings and the description to refer to the same or like parts.

As shown in drawings, the present invention relates to transtympanic vibration devices 100 and 200 and an apparatus 300 which is used when installing the transtympanic vibration devices 100 and 200 on a tympanic membrane 1, according to various embodiments and variations.

Referring to FIG. 1, the transtympanic vibration device 100 according to an embodiment of the present invention can be installed adjacent to the lower end of the tympanic membrane 1 below the manibrium of a malleus 2. The transtympanic vibration device 100 is vibrated by the magnetic flux transmitted from an outside and directly transfers the vibration to the tympanic membrane 1. In the external auditory canal 3 of an ear, there is disposed an outside coil 10 for generating magnetic flux in the form of electromagnetic waves.

The outside coil 10 functions to convert sound into magnetic flux having a corresponding density and transmit the magnetic flax to the transtympanic vibration device 100. Since the outside coil 10 is well known in the art and does not constitute the features of the present invention, the detailed description thereof will be omitted herein.

Figure 2:
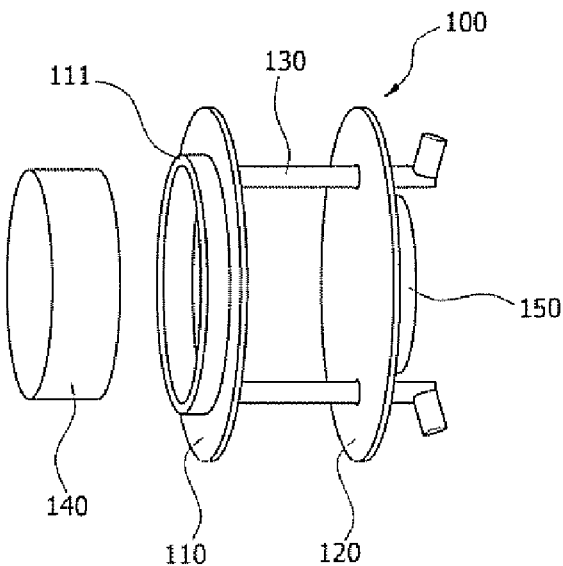
FIG. 2 is a perspective view illustrating a transtympanic vibration device in accordance with an embodiment of the present invention.

FIG. 2 is a perspective view illustrating the transtympanic vibration device 100 in accordance with the embodiment of the present invention. Referring to FIG. 2, the transtympanic vibration device 100 generally includes an outer plate 110, an inner plate 120, and connection members 130.

The outer plate 110 is positioned on the outer surface of the tympanic membrane 1 which faces the external auditory canal 3 of the ear. A detachable magnet 140 is detachably arranged on the outer surface of the outer plate 110. At this time, it is preferred that a mounting part 111 having a size corresponding to that of the detachable magnet 140 is formed on the outer plate 110 such that the detachable magnet 140 can be easily arranged on the mounting part 111.

While the mounting part 111 can have various sectional shapes, it must have a sectional shape corresponding to that of the detachable magnet 140. Therefore, if the detachable magnet 140 has a quadrangular sectional shape, the mounting part 111 has a quadrangular sectional shape. If the detachable magnet 140 has a circular sectional shape as shown in the drawing, the mounting part 111 has a circular sectional shape.

The detachable magnet 140 can be attached to or detached from the outer plate 110 as the occasion demands. The attachment and detachment of the detachable magnet 140 are performed by the apparatus 300 for installing a transtympanic vibration device in accordance with another embodiment of the present invention which will be described later.

The inner plate 120 is positioned on the inner surface of the tympanic membrane 1 which faces the middle ear cavity 4 of the ear such that the tympanic membrane 1 can be sandwiched between the outer plate 110 and the inner plate 120. A fixed magnet 150 is arranged on the inner surface of the inner plate 120.

Unlike the detachable magnet 140 described above, the fixed magnet 150 is fixedly coupled to the inner plate 120. If the detachable magnet 140 is arranged on the outer plate 110 with the fixed magnet 150 fixedly coupled to the inner plate 120, attractive force is created between the fixed magnet 150 and the detachable magnet 140, and the distance between the outer plate 110 and the inner plate 120 decreases. Hence, the transtympanic vibration device 100 according to the embodiment of the present invention can be securely held on the tympanic membrane 1 between the outer plate 110 and the inner plate 120.

The size and the magnetic force of the fixed magnet 150 can be set such that the magnetic force thereof can reach the external auditory canal 3 through the tympanic membrane 1.

Since the outer plate 110 and the inner plate 120 come into direct contact with the tympanic membrane 1, it is preferred that they be made of a bio-compatible material such as titanium.

The connection members 130 function to connect the outer plate 110 and the inner plate 120 in a manner such that the distance between the outer plate 110 and the inner plate 120 can be adjusted.

The connection members 130 are installed such that they are fixedly coupled to any one of and movably pass through the other of the outer plate 110 and the inner plate 120. Referring to FIG. 2, the connection members 130 are fixedly coupled to the outer plate 110 and movably pass through the inner plate 120 so that the distance between the outer plate 110 and the inner plate 120 can be adjusted.

Figure 3A:
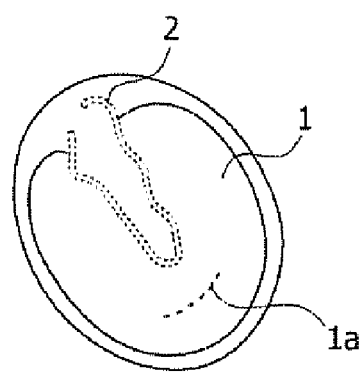
FIGS. 3A through 3C are views illustrating the state in which the device of FIG. 2 is installed adjacent to the lower end of a tympanic membrane below the manibrium of a malleus as in FIG. 1.
Figure 3B:
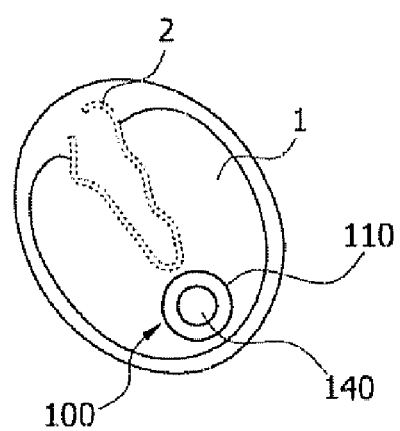
Figure 3C:
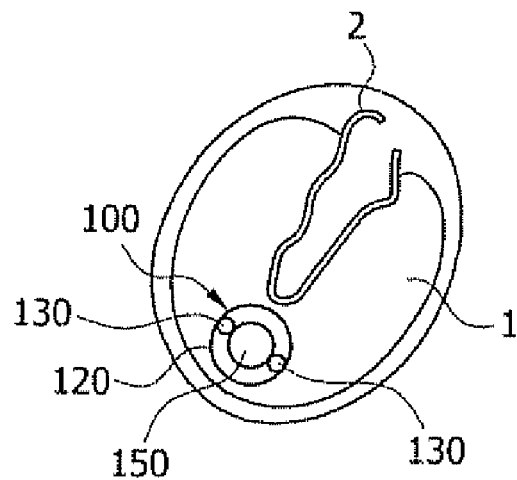

FIGS. 3A through 3C are views illustrating the state in which the transtympanic vibration device is installed adjacent to the lower end of the tympanic membrane 1 below the manibrium of the malleus 2 as in FIG. 1, wherein FIG. 3A shows the incised portion of the tympanic membrane 1 through which the transtympanic vibration device 100 is to be installed. FIG. 3B shows the transtympanic vibration device 100 which is installed on the tympanic membrane 1 and viewed from the external auditory canal 3, and FIG. 3C shows the transtympanic vibration device 100 which is installed on the tympanic membrane 1 and viewed from the middle ear cavity 4.

In order to install the transtympanic vibration device 100 on the tympanic membrane 1 below the manibrium of the malleus 2, after incising the tympanic membrane 1 to a predetermined length as shown in FIG. 3A, the inner plate 120 is inserted through the incised portion 1a of the tympanic membrane 1 such that the inner plate 120 can be positioned in the middle ear cavity 4 and the outer plate 110 connected to the inner plate 120 by the connection members 130 can be positioned in the external auditory canal 3.

Then, as time goes by, the incised portion 1a of the tympanic membrane 1 recovers and is joined to the tympanic membrane 1 with the connection members 130 inserted through the tympanic membrane 1. The sectional shape in this state is shown in FIG. 4.

Figure 4:
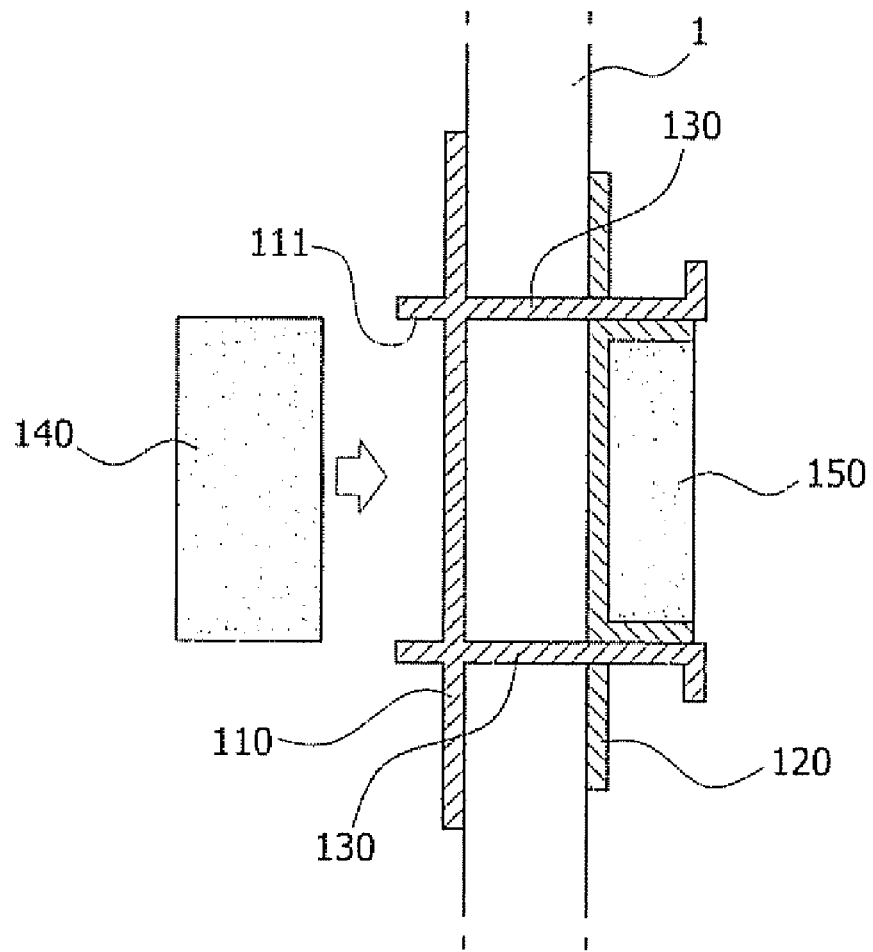
FIG. 4 is a sectional view corresponding to FIGS. 3A through 3C.

FIG. 4 is a sectional view corresponding to FIGS. 3A through 3C. Referring to FIG. 4, the outer plate 110 is positioned in the external auditory canal 3 and the inner plate 120 is positioned in the middle ear cavity 4 while the tympanic membrane 1 is interposed therebetween. The connection members 130 for connecting the outer plate 110 and the inner plate 120 pass through the tympanic membrane 1 such that the distance between the outer plate 110 and the inner plate 120 can be adjusted.

Because the fixed magnet 150 is arranged on the inner plate 120, if the detachable magnet 140 is inserted by the apparatus 300 for installing a transtympanic vibration device and is arranged on the outer plate 110, the outer plate 110 and the inner plate 120 can be stably attached to the tympanic membrane 1 by the attractive force produced between the fixed magnet 150 and the detachable magnet 140.

Figure 5:
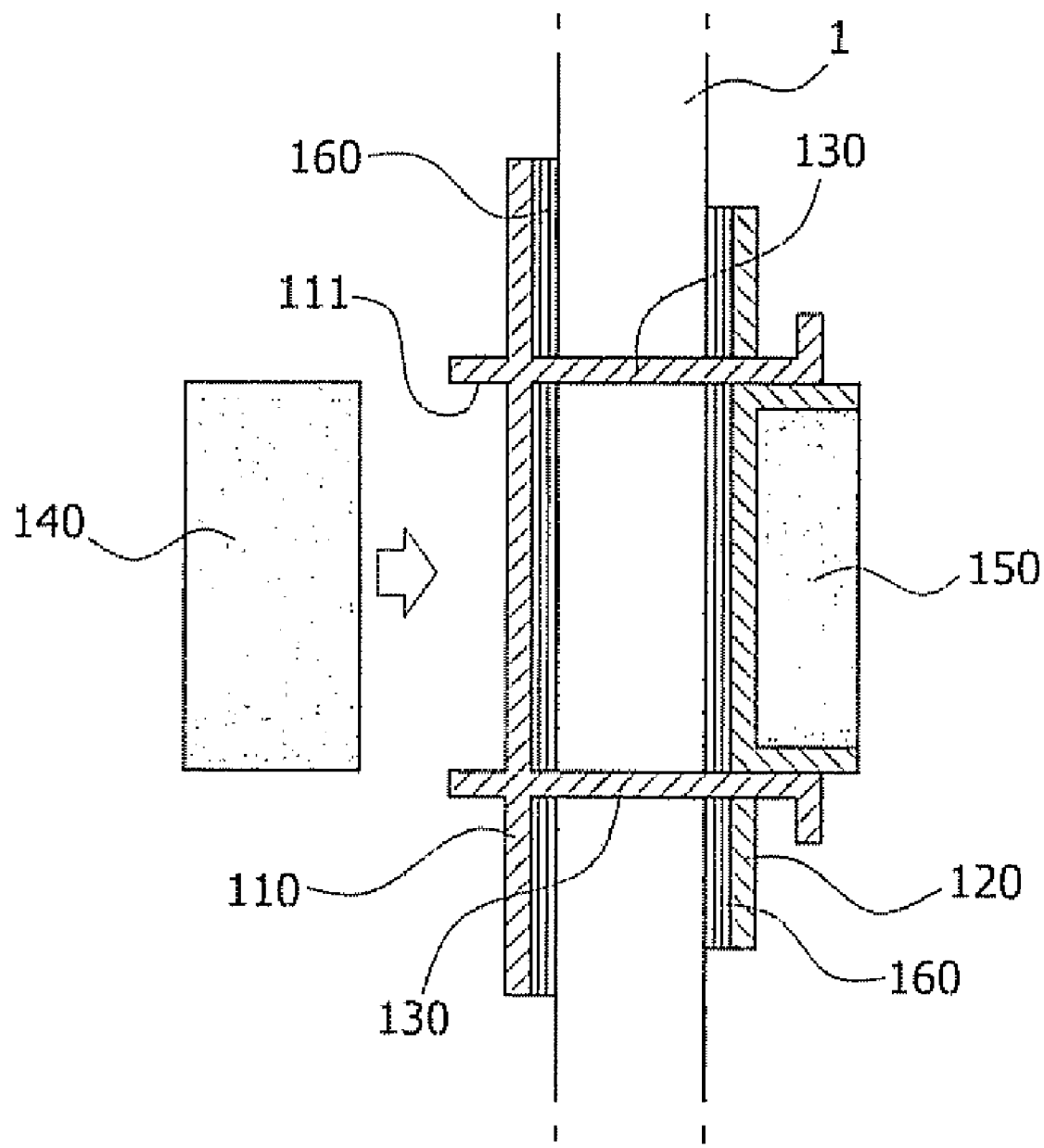
FIG. 5 is a sectional view illustrating the state in which a soft substance is provided to the device shown in FIG. 4.

Meanwhile, because a user can feel pain due to the force applied to the tympanic membrane 1 when the outer plate 110 and the inner plate 120 are attached to the tympanic membrane 1, it is preferred that a soft substance 160 be provided on the surfaces of the outer plate 110 and the inner plate 120 which come into contact with the tympanic membrane 1 as shown in FIG. 5.

The soft substance 160 not only alleviates the pain of the tympanic membrane 1, but also allows the outer plate 110 and the inner plate 120 to come into contact with the tympanic membrane 1 while under a high adhesive force. The soft substance 160 can comprise silicon having high flexibility or a mineral oil layer having high viscosity.

Figure 6:
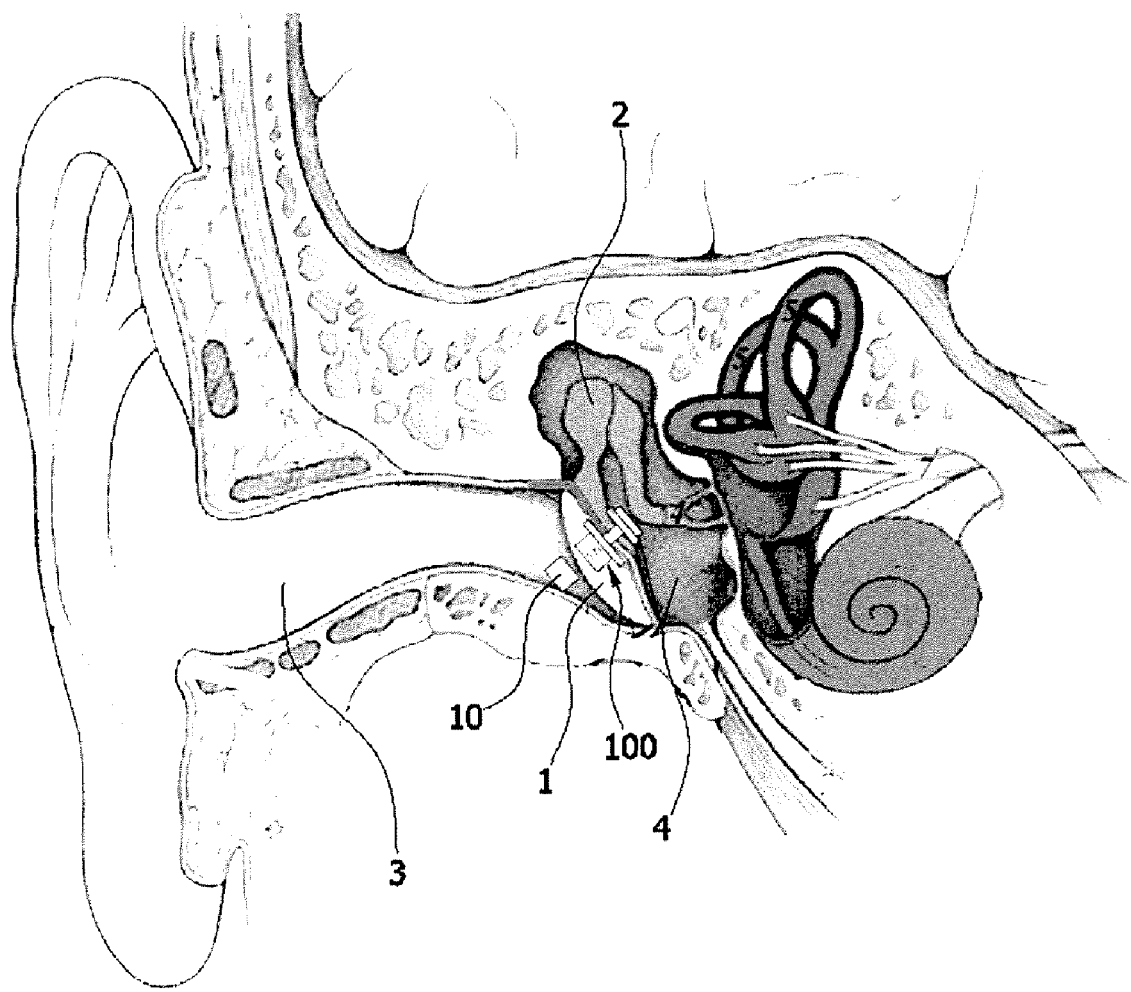
FIG. 6 is a view illustrating the state in which a transtympanic vibration device according to the present invention is installed on a tympanic membrane and partially or wholly on the manibrium of a malleus.
Figure 7A:
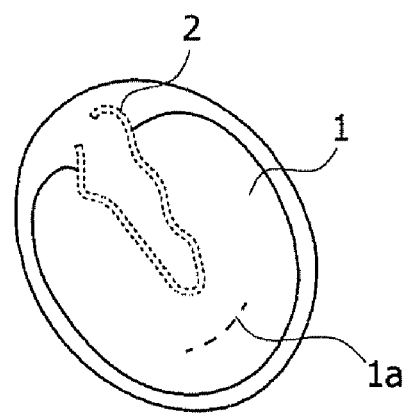
FIGS. 7A through 7C are views illustrating the state in which the device according to the present invention is installed partially on the manibrium of a malleus.
Figure 7B:
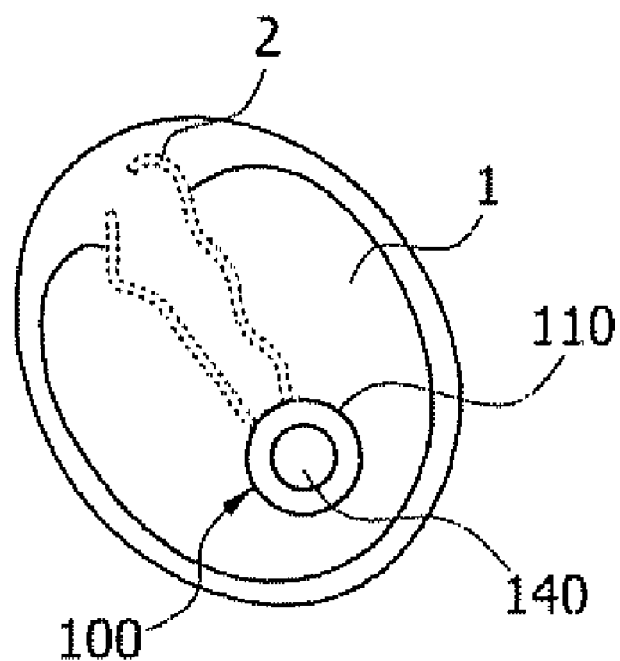
Figure 7C:
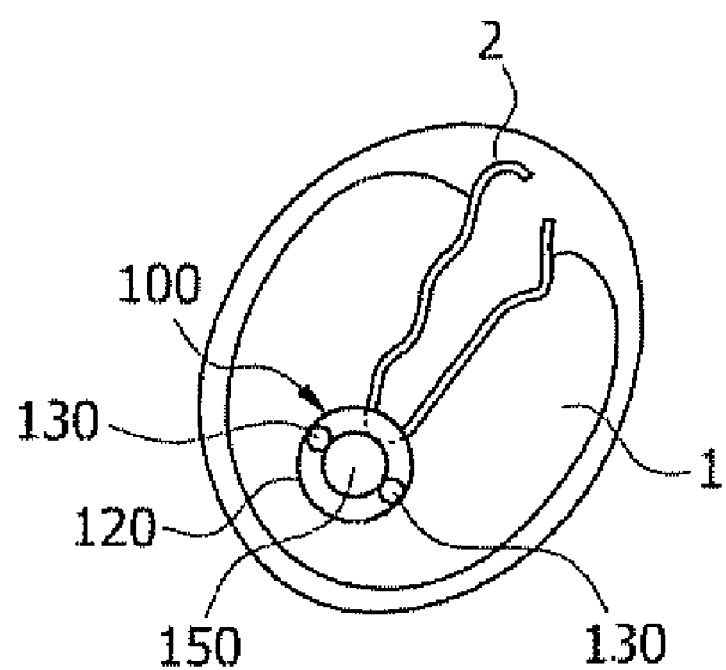
Figure 10A:
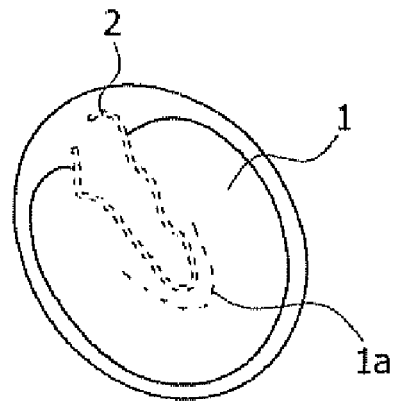
FIGS. 10A through 10C are views illustrating the state in which the device according to the present invention is installed wholly on the manibrium of a malleus.
Figure 10B:
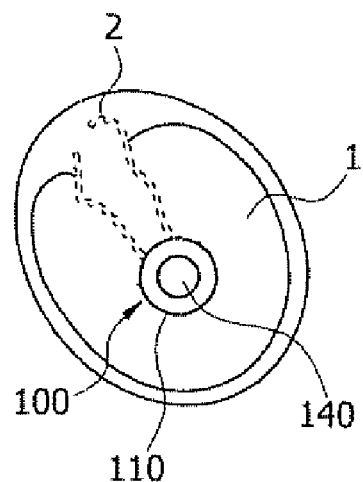
Figure 10C:
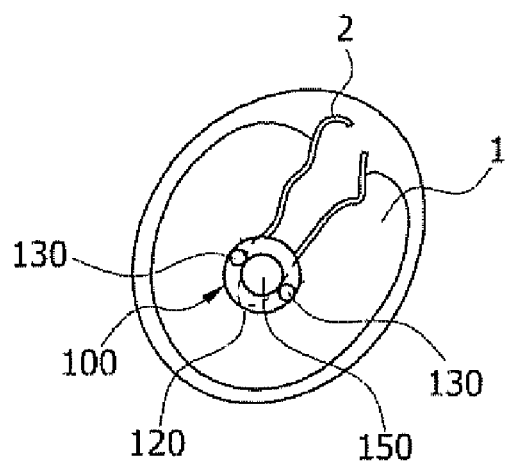
Figure 15A:
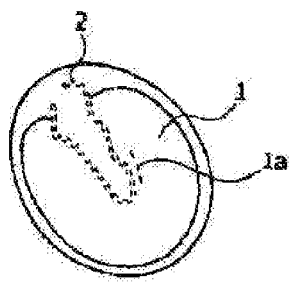
FIGS. 15A through 15C are views illustrating the state in which a transtympanic vibration device according to a variation of the present invention is coupled to the manibrium of a malleus through a clip element while minimizing the incision of a tympanic membrane.
Figure 15B:
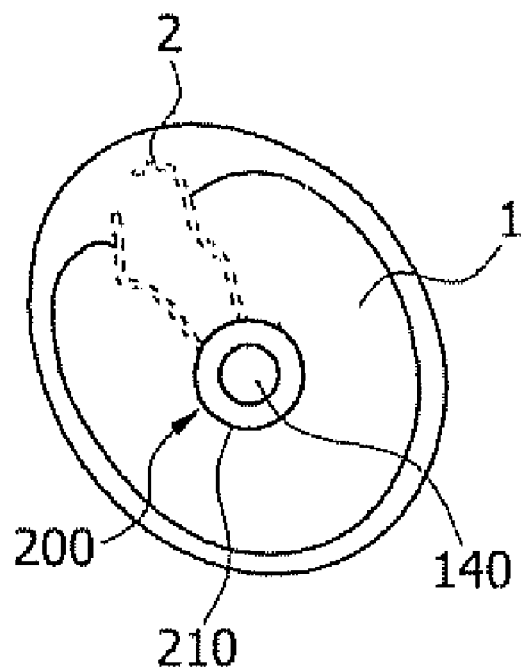
Figure 15C:
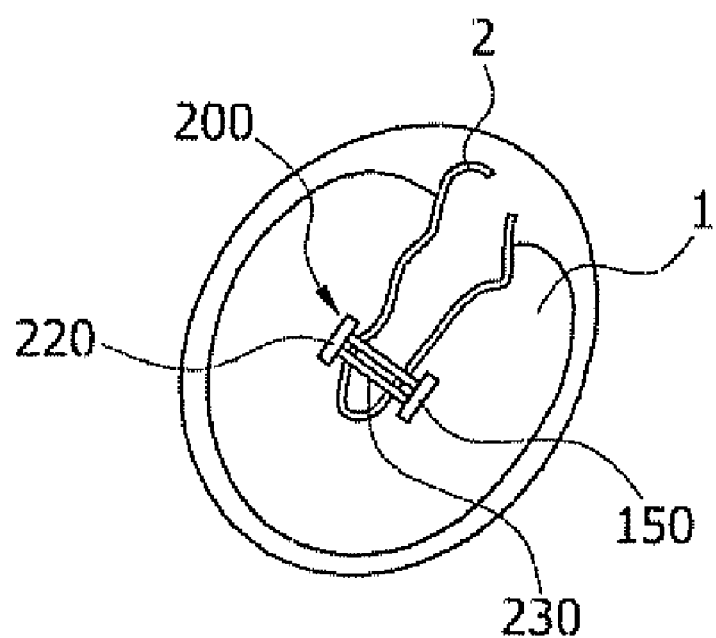

The transtympanic vibration device 100 according to the present invention can be installed not only on the tympanic membrane 1 but also partially or wholly on the manibrium of the malleus 2 as shown in FIG. 6. In this regard, FIGS. 7A through 7C are views illustrating the state in which the device 100 according to the present invention is installed partially on the manibrium of the malleus 2. FIGS. 10A through 10C are views illustrating the state in which the device 100 according to the present invention is installed wholly on the manibrium of the malleus 2, and FIGS. 15A through 15C are views illustrating the state in which the transtympanic vibration device 200 according to a variation of the present invention is coupled to the manibrium of the malleus 2 through a clip element while minimizing the size of the incised portion 1a of the tympanic membrane 1. FIGS. 7A, 10A and 15A show the incised portion 1a of the tympanic membrane 1 through which the transtympanic vibration device 100 or 200 is to be installed, FIGS. 7B, 10B and 15B show the transtympanic vibration device 100 or 200 which is installed on the tympanic membrane 1 and viewed from the external auditory canal 3, and FIGS. 7C, 10C and 15C show the transtympanic vibration device 100 or 200 which is installed on the tympanic membrane 1 and viewed from the middle ear cavity 4.

Figure 8:
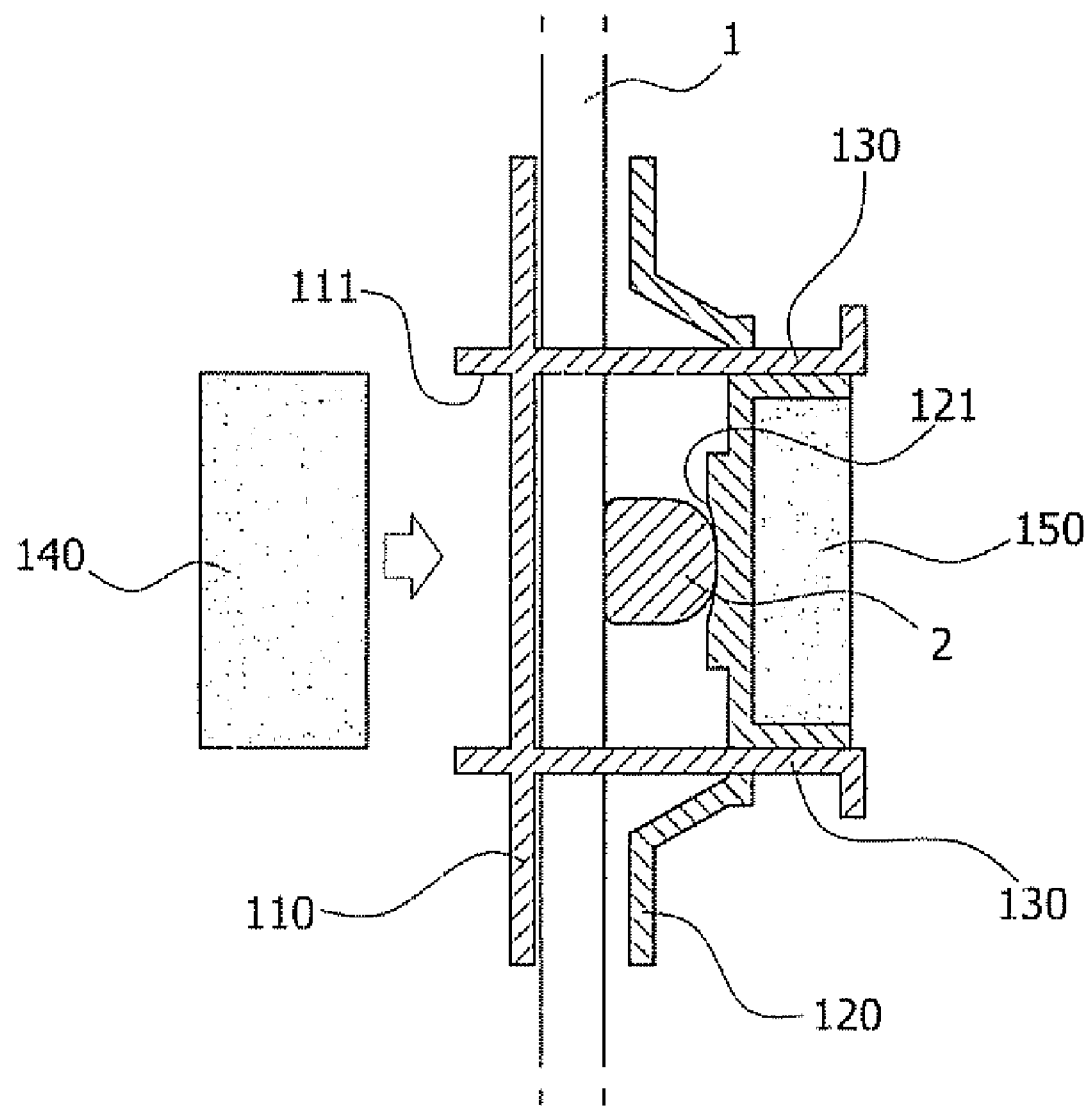
FIGS. 8 and 9 are sectional views corresponding to FIGS. 7A through 7C.
Figure 9:
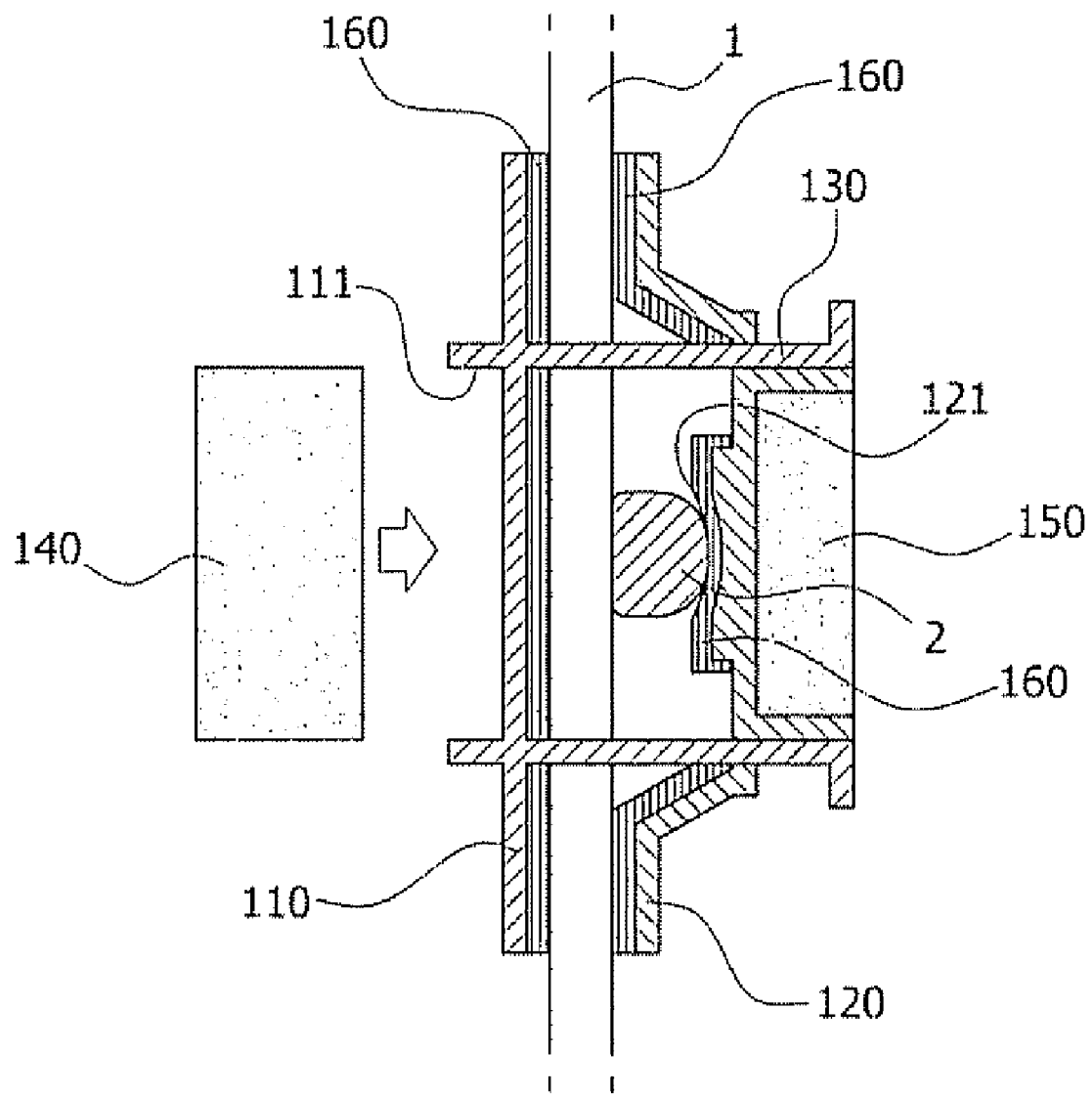

FIGS. 8 and 9 are sectional views corresponding to FIGS. 7A through 7C. Referring to FIG. 8, the tympanic membrane 1 and the manibrium of the malleus 2 are placed between the outer plate 110 and the inner plate 120. If the detachable magnet 140 is arranged on the outer plate 110, the distance between the outer plate 110 and the inner plate 120 is decreased such that the outer plate 110 and the inner plate 120 are closely attached to the tympanic membrane 1 and the manibrium of the malleus 2.

While the transtympanic vibration device 100 shown in FIG. 8 is basically similar to that shown in FIG. 4, the tympanic membrane 1 as well as the manibrium of the malleus 2 are placed between the outer plate 110 and the inner plate 120. In this regard, in order to allow the inner plate 120 to be stably and closely attached to the tympanic membrane 1, the peripheral portion of the inner plate 120 is bent toward the tympanic membrane 1.

It is preferred that a seating part 121 be formed on the outer surface of the inner plate 120 which comes into contact with the manibrium of the malleus 2, so as to increase the contact area between the inner plate 120 and the malleus 2.

For reference, because the surface of the manibrium of the malleus 2, which comes into contact with the inner plate 120, is somewhat rounded, in order to increase the contact area, it is preferred that the surface of the seating part 121, which comes into contact with the manibrium of the malleus 2, be formed to have a curvature corresponding to the curvature of Hie manibrium of the malleus 2.

Of course, even at this time, it is preferred that the aforementioned soft substance 160 be provided on the surfaces of the outer plate 110 and the inner plate 120 which come into contact with the tympanic membrane 1 and the manibrium of the malleus 2 as shown in FIG. 9, such that the user does not feel pain when the outer plate 110 and the inner plate 120 are closely attached to the tympanic membrane 1 and the manibrium of the malleus 2.

Figure 11A:
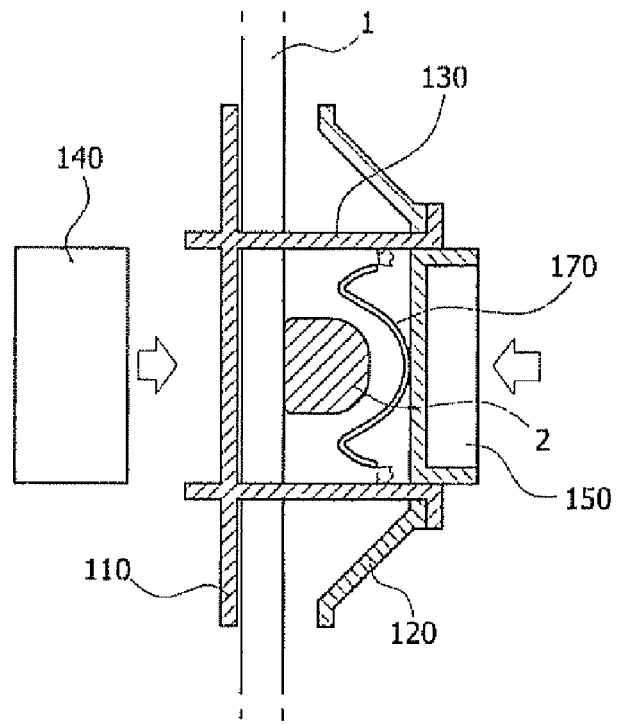
FIGS. 11A and 11B are sectional views corresponding to FIGS. 10A through 10C.
Figure 11B:
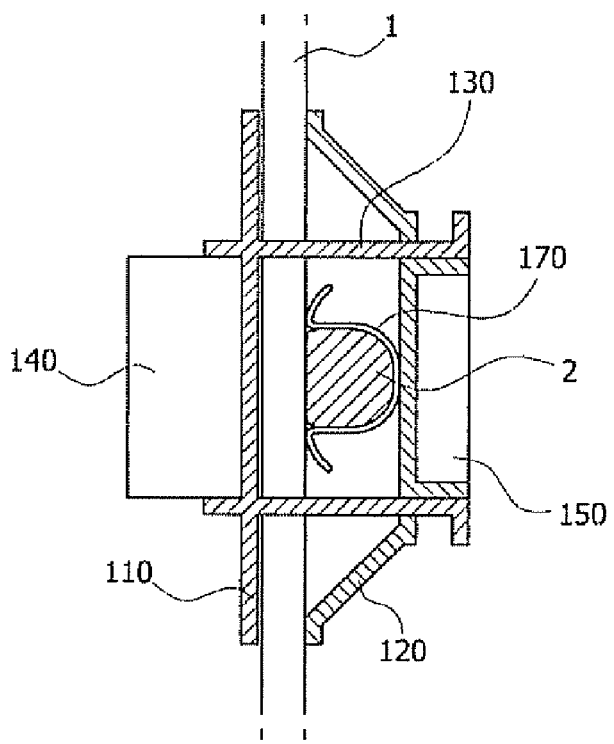

FIGS. 11A and 11B are sectional views corresponding to FIGS. 10A through 10C in which the transtympanic vibration device 100 according to the present invention is installed wholly on the manibrium of the malleus 2. While the transtympanic vibration device 100 shown in FIGS. 11A and 11B is substantially similar to that shown in FIG. 8, a clip element 170 is installed on the outer surface of the inner plate 120 to be coupled to the malleus 2 so that the device can be stably held on the manibrium of the malleus 2.

The shape of the clip element 170 is not limited specifically as long as it can be coupled to the manibrium of the malleus 2. Since the clip element 170 comes into direct contact with the manibrium of the malleus 2, it is preferred that the clip element 170 be made of a bio-compatible material capable of elastic deformation.

The clip element 170 is initially kept sufficiently diverged as shown in FIG. 11A in consideration of the size of the manibrium of the malleus 2. The diverging of the clip element 170 is enabled by the magnetic force of the fixed magnet 150. Namely, the clip element 170 is kept diverged before the detachable magnet 140 is arranged on the outer plate 110.

In this state, if the detachable magnet 140 is arranged on the outer plate 110, the magnetic force of the detachable magnet 140 and the magnetic force of the fixed magnet 150 offset each other, and therefore, the clip element 170 converges due to the elastic returning force thereof and is securely fixed to the manibrium of the malleus 2 as shown in FIG. 11B.

While the clip element 170 can repeat the diverging and the converging by the magnetic force of the fixed magnet 150 and the elastic returning force thereof, it can be envisaged in another embodiment that the clip element 170 is made of a shape memory material which can converge by the application of heat.

In the case where the clip element 170 is made of the shape memory material, when the clip element 170 is brought into contact with the manibrium of the malleus 2, the clip element 170 converges by the heat transferred from the manibrium of the malleus 2 and is securely coupled to the manibrium of the malleus 2 as shown in FIG. 11B.

It is preferred that at least two connection members 130 be provided to be spaced apart by a predetermined interval on the outer plate 110 and the inner plate 120. In the case where two connection member's 130 are provided as shown in the drawings, the connection members 130 are preferably installed to be spaced apart by 180° such that the outer plate 110 and the inner plate 120 can be stably connected with each other by the connection members 130.

Figure 12A:
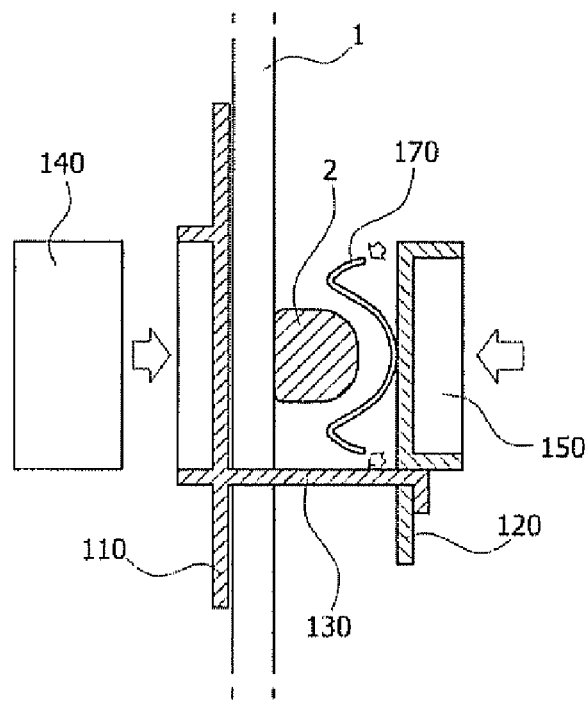
FIGS. 12A and 12B are views illustrating the case where a single connection member is used.
Figure 12B:
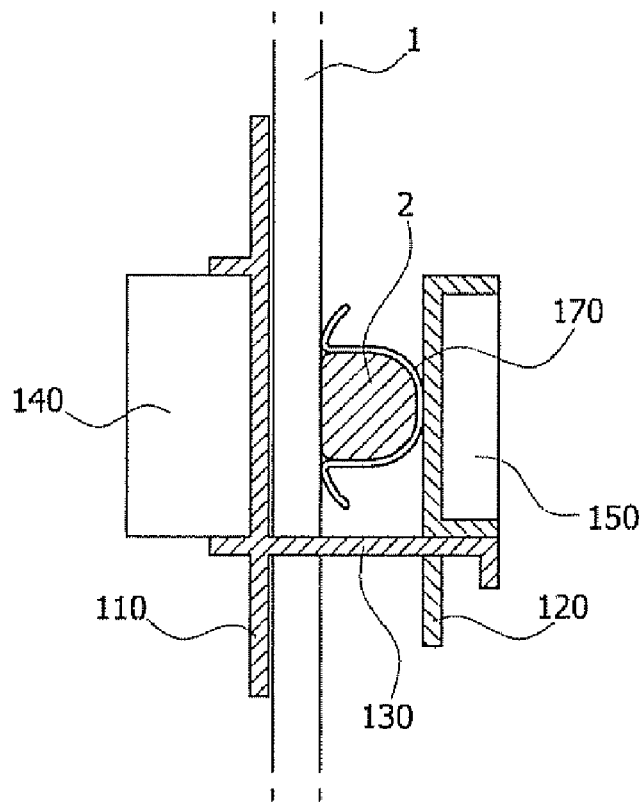

Also, only one connection member 130 can be provided as shown in FIGS. 12A and 12B. In this case, while stability may decrease when compared to the aforementioned case where two connection members 130 are provided, a problem does not occur as long as the manibrium of the malleus 2 can be securely grasped by the clip element 170. In particular, since only one connection member 130 is provided, the construction can be simplified and a light weight can be attained when compared to the case where two connection member's 130 are provided.

The thickness and the surface contour of the tympanic membrane 1 may vary from person to person. In this connection, if the transtympanic vibration device 100 is installed at such a position shown in FIGS. 10A through 10C, the tympanic membrane 1 is likely to be uneven and may have a non-uniform surface contour.

Figure 13:
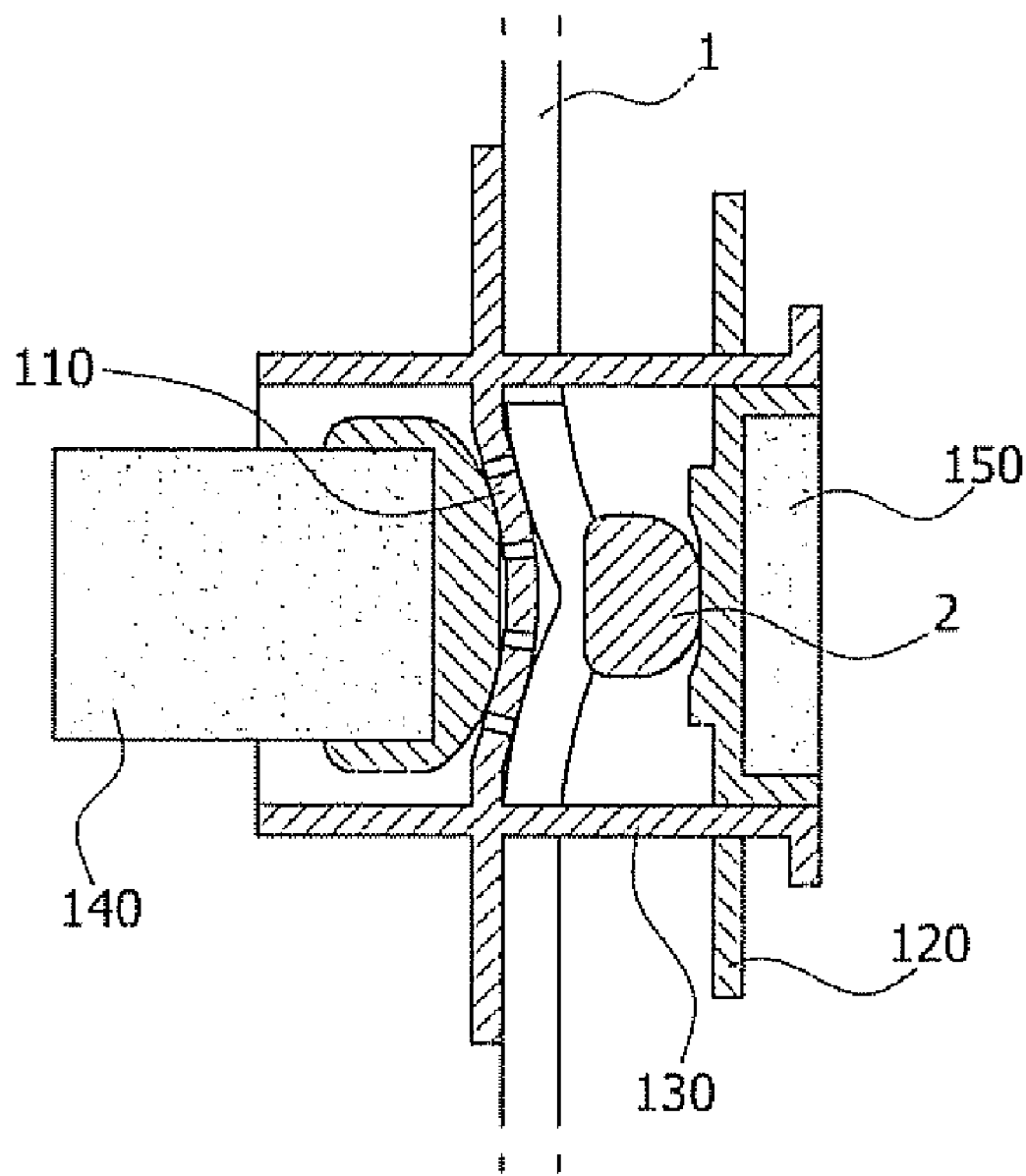
FIGS. 13 and 14 are views illustrating the variations of the present invention that can be applied to tympanic membranes having various surface contours.
Figure 14A:
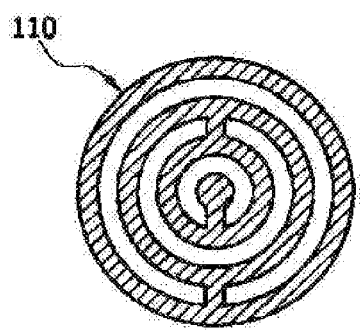
Figure 14B:
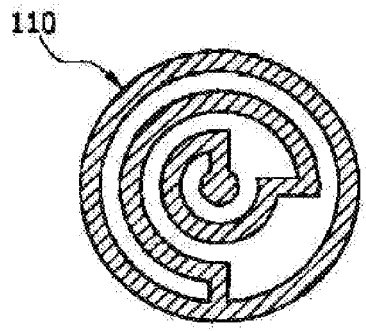
Figure 14C:
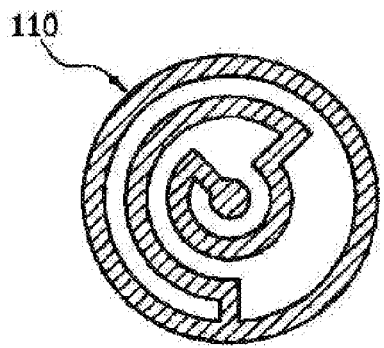
Figure 14D:
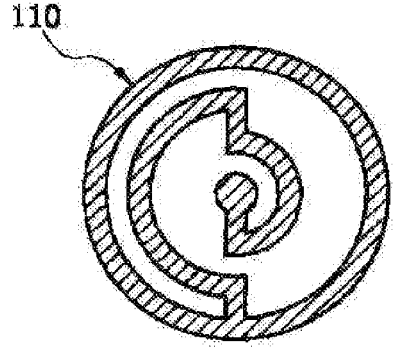

Thus, when the tympanic membrane 1 having the non-uniform surface contour projects toward the middle ear cavity 4 as shown in FIG. 13, it is preferred that the outer plate 110 be formed as a thin soft layer so as to improve the adhesion of the outer plate 110 to the tympanic membrane 1.

If the portion of the outer plate 110, which comes into contact with the tympanic membrane 1 having a certain surface contour, is formed as a thin soft layer, because the elastic deformation force increases and the outer plate 110 can be deformed to conform to the surface contour of the tympanic membrane 1, the contact surface therebetween can be increased. According to this, the transtympanic vibration device 100 can be stably installed on the tympanic membrane 1 which has a surface contour varying from person to person.

Further, when the tympanic membrane 1 having a certain surface contour projects toward the middle ear cavity 4, the outer plate 110 can comprise various spiral plates as shown in FIG. 14, each of which has a diameter gradually decreasing toward the center thereof.

That is to say, if the outer plate 110 comprises various spiral plates as exemplified in FIG. 14, since the outer plate 110 can be deformed into various shapes, the outer plate 110 can easily conform to the specific surface contour of the tympanic membrane 1.

Figure 16A:
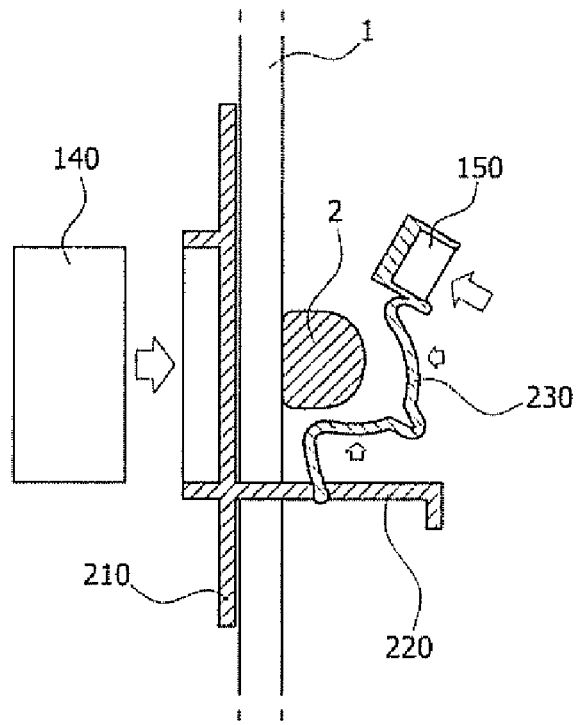
FIGS. 16A and 16B are sectional views corresponding to FIGS. 15A through 15C.
Figure 16B:
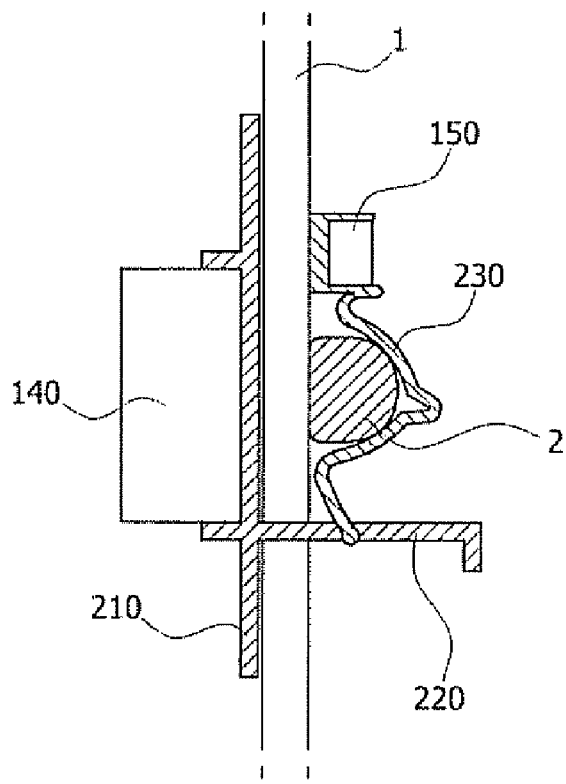

FIGS. 15A through 15C are views illustrating the state in which the transtympanic vibration device 200 according to a variation of the present invention is coupled to the manibrium of the malleus 2 through a clip element while minimizing the size of the incised portion la of the tympanic membrane 1. FIGS. 16A and 16B are sectional views corresponding to FIGS. 15A through 15C.

Referring to FIGS. 16A and 16B, the transtympanic vibration device 200 according to the variation of the present invention includes an outer plate 210, an extended part 220, and a clip element 230.

As aforementioned above, the outer plate 110 is positioned on the surface of the tympanic membrane 1 which faces the external auditory canal 3, and a detachable magnet 140 is detachably arranged on the outer surface of the outer plate 110.

The extended part 220 extends from the outer plate 210 through the tympanic membrane 1 into the middle ear cavity 4 by a predetermined length. The extended part 220 is formed as a single element as shown in the drawing.

The clip element 230 has predetermined elastic returning force. One end of the clip element 230 is coupled to the extended part 220 such that it is elastically diverged outward, and a fixed magnet 150 is arranged on the other end of the clip element 230. Thus, the clip element 230 can converge by the attractive force produced between the detachable magnet 140 arranged on the outer plate 210 and the fixed magnet 150 and can thereby be coupled to the manibrium of the malleus 2.

If the detachable magnet 140 is removed from the outer plate 110, the clip element 230 diverges again into the original shape because of its elastic returning force. Thus, with the clip element 230 diverged, the transtympanic vibration device 200 can be removed from the tympanic membrane 1 and the manibrium of the malleus 2.

Figure 17:
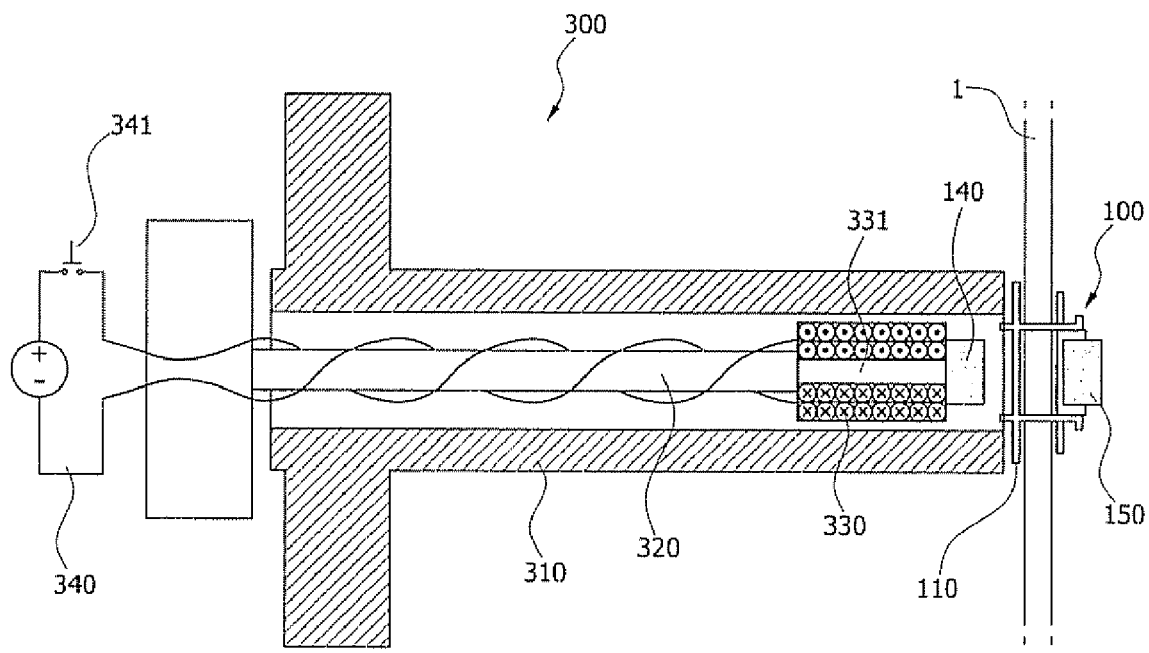
FIG 17 is a view illustrating the construction of an apparatus for installing a transtympanic vibration device, in accordance with another embodiment of the present invention.

Meanwhile, in order to install the above-described transtympanic vibration devices 100 and 200 according to the embodiment and the variations of the present invention on the tympanic membrane 1, the separate installation apparatus 300 as shown in FIG. 17 is needed. The apparatus 300 for installing a transtympanic vibration device in accordance with another embodiment of the present invention is provided to install and remove the transtympanic vibration device 100 or 200 onto and off from the tympanic membrane 1. The apparatus 300 generally includes a guide member 310, a movable member 320, a magnetic force production part 330, and a power source part 340.

The guide member 310 has a diameter to be introduced into the ear hole of the user and a length which can extend from the ear hole to the tympanic membrane 1. The guide member 310 has a hollow configuration.

It is preferred dial the inner diameter of the guide member 310 be the same as or slightly greater than the outer diameter of the mounting part 111 which is formed on the outer plate 110 of the transtympanic vibration device 100.

The movable member 320 is inserted into the guide member 310 to be moved along the guide member 310 toward the tympanic membrane 1, and the magnetic force production part 330 is installed on the distal end of the movable member 320.

The magnetic force production part 330 is constructed such that it is supplied with electric power from an outside, is magnetized and produces magnetic force. While there are various ways of producing magnetic force, in the present invention, the magnetic force production part 330 comprises a magnetized coil.

Therefore, if power is supplied to the magnetic force production part 330, the magnetic force production part 330 becomes an electromagnet. In this state, the detachable magnet 140 is attached to the magnetic force production pail 330 and is moved inward to be arranged on the outer plate 110 of the transtympanic vibration device. When the detachable magnet 140 is arranged on the outer plate 110, by interrupting the power supply to the magnetic force production part 330, the detachable magnet 340 is detached from the magnetic force production part 330. In this way, the detachable magnet 140 can be easily arranged on the outer plate 13 0.

When it is necessary to remove the detachable magnet 140 from the outer plate 110, the magnetic force production part 330 is moved adjacent to the detachable magnet 140 in the same manner. In this state, by supplying power to the magnetic force production part 330, the detachable magnet 140 is attached again to the magnetic force production part 330.

It is preferred that a paramagnet 331 such as a ferrite core be embedded in the center portion of the magnetic force production part 330 so that lines of magnetic force can be gathered to maximize the production of magnetic force.

In order to supply electric power to the magnetic force production part 330, the power source part 340 is provided such that it is electrically connected with the magnetic force production part 330.

Preferably, a switch 341 is provided to the power source part 340 to enable easy control of the power supply.

The transtympanic vibration device and the apparatus for installing the same on a tympanic membrane according to Ore present invention provide advantages as described below.

First, since a scheme for directly vibrating the tympanic membrane is adopted instead of the conventional scheme for transmitting sound in an air conduction type hearing aid, the vibration efficiency of high frequency signal components can be elevated. Due to this fact, speech discrimination of a person who has difficulties in hearing in noisy circumstances can be improved, and the sensorineural hearing loss at high frequency as the general form of presbycusis can be effectively compensated for.

Second, in the present invention, since the natural healing of the tympanic membrane is used, a separate bonding material or an elaborate and risky operation such as drilling of the ear ossicles is not needed nor required when compared to the conventional vibration device installed on a tympanic membrane. Also, even though the thickness and the surface contour of the tympanic membrane vary from person to person, since the device has a structure which can be installed to come into close contact with both inner and outer surfaces of the tympanic membrane, coupling force between the device and the tympanic membrane can be stably and reliably produced.

Third, in the present invention, a sound having a high gain can be directly transferred to a middle ear through the vibration of the tympanic membrane. Accordingly, by using the transtympanic vibration device according to the present invention, the speech discrimination of persons who have intermediate and extreme hearing loss can be significantly improved Fourth, in the present invention, due to the fact that a clip element made of a material having flexibility or a material having a shape memory characteristic is employed, the device can be stably coupled to the tympanic membrane.

Fifth, in the apparatus for installing a transtympanic vibration device according to the present invention, when installing and removing the device on and from the tympanic membrane, substantial physical force is not applied to the tympanic membrane and the ear ossicles, by which the precise installation of the device becomes possible.

Although preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A transtympanic vibration device for an implantable hearing aid, suitable for being vibrated by magnetic flux transmitted from an outside and for transferring vibration to a tympanic membrane, the device comprising.
    an outer plate having one surface on which a detachable magnet is detachably arranged;
    an inner plate for sandwiching the tympanic membrane in cooperation with the outer plate and having a surface on which a fixed magnet is arranged; and at least one connection member connecting the outer plate and the inner plate with each other in such a manner that a distance between the outer plate and the inner plate can be adjusted,
    wherein a clip element is installed on an outer surface of the inner plate to be coupled to a malleus, wherein the clip element is kept elastically diverged by the magnetic force of the fixed magnet plate and converges and is coupled to the malleus when the detachable magnet is arranged on the outer plate.

2. The transtympanic vibration device according to claim 1, wherein magnetic force of the fixed magnet is for being applied to an external auditory canal through the tympanic membrane.

3. The transtympanic vibration device according to claim 1, wherein a mounting part is formed on the outer plate to allow the detachable magnet to be arranged thereon.

4. The transtympanic vibration device according to claim 3, wherein the connection member is installed to be securely fastened to one of the outer plate and the inner plate and to pass through the other of the outer plate and the inner plate.

5. The transtympanic vibration device according to claim 4, wherein a soft substance is provided to surfaces of the outer plate and the inner plate which come into contact with the tympanic membrane during use.

6. The transtympanic vibration device according to claim 5, wherein a seating part is formed on an outer surface of the inner plate to increase a contact area between the inner plate and a malleus.

7. The transtympanic vibration device according to claim 1, wherein the clip element is made of a shape memory material which converges because of heat from a human body.

8. The transtympanic vibration device according to claim 6, wherein, when the tympanic membrane projects toward a middle ear cavity, the outer plate comprises a thin soft layer for increasing adhesive force between the outer plate and the tympanic membrane having a certain surface contour.

9. The transtympanic vibration device according to claim 6, wherein, when the tympanic membrane projects toward a middle ear cavity, the outer plate comprises a spiral plate which has a diameter gradually decreasing toward a center thereof.

10. The transtympanic vibration device according to claim 1, wherein at least two connection members are provided on the outer plate and the inner plate so as to be spaced apart by a predetermined interval.

11. The transtympanic vibration device according to claim 1, wherein one connection member is provided.

12. An apparatus for installing or removing the transtympanic vibration device according to claim 1 on or from a tympanic membrane, the apparatus comprising;:
    a hollow guide member having a length that extends from an ear hole to the tympanic membrane; a movable member inserted into the guide member; a magnetic force production part installed on a distal end of the movable member and producing magnetic force when electric power is applied thereto; and
    a power source part supplying electric power to the magnetic force production part.

13. The apparatus according to claim 12, wherein a paramagnet is embedded in a center portion of the magnetic force production part to gather lines of magnetic force.

14. The transtympanic vibration device according to claim 7, wherein at least two connection members are provided on the outer pate and the inner plate so as to be spaced apart by a predetermined interval.

* * * * *